United States Patent [19]

Chapuis

[11] Patent Number: 5,300,716
[45] Date of Patent: Apr. 5, 1994

[54] PROCESS FOR THE PREPARATION OF POLYUNSATURATED OLEFINS

[75] Inventor: Christian Chapuis, Mies, Switzerland

[73] Assignee: Firmenich SA, Geneva, Switzerland

[21] Appl. No.: 755,719

[22] Filed: Sep. 6, 1991

[30] Foreign Application Priority Data

Oct. 3, 1990 [CH] Switzerland .................. 3181/90

[51] Int. Cl.$^5$ .................. C07C 5/05; C07C 2/02
[52] U.S. Cl. .................. 585/277; 585/310; 585/506; 585/507; 585/508; 585/600
[58] Field of Search ............... 585/271, 310, 506, 507, 585/508, 600

[56] References Cited

U.S. PATENT DOCUMENTS

| | | |
|---|---|---|
| 3,532,762 | 10/1970 | Corbier et al. . |
| 3,960,977 | 6/1976 | Naf et al. . |
| 4,014,951 | 3/1977 | Naf et al. . |
| 4,467,118 | 8/1984 | Chalk et al. . |
| 4,652,692 | 3/1987 | Fugier et al. . |

FOREIGN PATENT DOCUMENTS

| | | |
|---|---|---|
| 203615 | 3/1986 | European Pat. Off. . |
| 0203615 | 12/1986 | European Pat. Off. . |
| 1668681 | 9/1971 | Fed. Rep. of Germany . |
| 7419580 | 3/1975 | France . |
| 2309498 | 11/1976 | France . |
| 681077 | 1/1968 | South Africa . |

OTHER PUBLICATIONS

Boland, et al., Stereospecific Synthesis and Spectroscopic Properties of Isomeric 2,4,6,8–Undecatetraenes. New Hydrocarbons from the Marine Brown Alga *Giffordia mitchellae*, Helv. Chim. Acta 70 1025 (1987).

Raetovelomanana et al., Synthese des undecatrienes-1,-3-5 naturels, Bull. Soc. Chim. Fr. 1, 174 (1987).

Block, et al., α–Haloalkanesulfonyl Bromides in Organic Synthesis.5. Verstile Reagents for the Synthesis of Congugated Polyenes, Enones, and 1,3–Oxathiole 1,1–Dioxides, J. Am. Chem. Soc. 108, 4568 (1986).

Näf, et al., The Four Isomeric 1,3,5–Undecatrienes. Synthesis and Configurational Assignment, Helv. Chim. Acta 58, 1016 (1975).

Teisseire, et al., syntheses d'undecatrienes, substances caracteristiques de l'huile essentielle de galbanum, Recherches 16, 5 (1967).

*Primary Examiner*—Patrick P. Garvin
*Assistant Examiner*—E. D. Irzinski
*Attorney, Agent, or Firm*—Pennie & Edmonds

[57] ABSTRACT

A process for the preparation of a polyunsaturated olefinic compound, i.e. undeca-1,3,5-triene, in its (3E,5Z) isomeric form, consisting of four consecutive steps starting from deca-1,4-diyne, is disclosed.

Said process has the advantage of making it possible to obtain the desired isomer in its essentially pure form.

9 Claims, No Drawings

PROCESS FOR THE PREPARATION OF POLYUNSATURATED OLEFINS

BRIEF SUMMARY OF THE INVENTION

The present invention relates to the perfume industry. It concerns, in particular, a process for the preparation of a polyunsaturated olefinic compound, undeca-1,3,5-triene, a much appreciated perfuming ingredient.

Said process comprises the following consecutive steps:
a. conversion of deca-1,4-diyne into a N,N-disubstituted undeca-2,5-diynylamine by way of treatment of said deca-1,4-diyne with formaldehyde and a secondary amine under the conditions of a Mannich type reaction; followed by
b. reduction of the thus obtained compound by means of a catalytic hydrogenation to give a N,N-disubstituted undeca-2Z,5Z-dienyl-amine; and
c. an elimination reaction, under the conditions of a so-called Hoffmann type reaction, consisting in the quaternarization of the obtained N,N-disubstituted undeca-2Z,5Z-dienyl-amine, conversion into the corresponding ammonium hydroxide and decomposition; or
d. conversion of said N,N-disubstituted undeca-2Z,5Z-dienyl-amine into the corresponding N-oxide; and
e. thermal treatment of the obtained N-oxide to give the desired undeca-1,3E,5Z-triene.

Another object of the present invention is a N,N-disubstituted undeca-2,5-diynyl-amine of formula

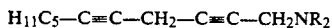

wherein R represents a lower alkyl radical and, in particular, N,N-diethyl-undeca-2,5-diynyl-amine.

Yet a further object of the invention is a process for the preparation of undeca-1,3E,5Z-triene, wherein
i. deca-1,4-diyne is reacted with an alkyl magnesium halide and then formaldehyde to give undeca-2,5-diyn-1-ol;
ii. the said diynol is subjected to catalytic hydrogenation to give undeca-2Z,5Z-dienol;
iii. the thus formed dienol is converted into undeca-2Z,5Z-dienyl chloride; and
iv. the latter compound is subjected to an elimination reaction by means of a basic agent consisting of an alkali metal alkoxide.

BACKGROUND OF THE INVENTION

There have been many proposed ways of synthesizing undeca-1,3,5-triene [see, for example, patent FR 74 19580; patent AS 68 01077; patent application EP 203 615; F. Naef et al., Helvetica Chimica Acta 1975, 58, 1016; V. Ratovelomanana et al.; Bull. Soc. Chim. Fr. 1987, 174; Recherches 1967, 16, 5; W. Boland et al., Helv. Chim. Acta 1987, 70, 1025; E. Block et al., J. Amer. Chem. Soc. 1986, 108, 4568] ever since its discovery [see: Chrétien-Bessière et al., Bull. Soc. Chim. Fr. 1967, 97]. Amongst the methods proposed, there are some which have found an industrial application and undeca-1,3,5-triene is presently commercialized under several tradenames. Since it is characterized by the presence of three ethylenic double bonds in its molecule, undeca-1,3-5-triene can take several isomeric forms, the respective proportions of which in the final product determine its olfactive quality. We have been able to establish that none of the described prior art methods can, at once, satisfy the economic, safety and environmental requirements and provide an irreproachable quality product, of better quality than that of the product currently avialable on the market.

The process of the present invention has the advantage of providing undeca-1,3,5-triene under its essentially pure undeca-1,3E,5Z-triene isomeric form. It is precisely this isomer which best develops the most characteristic and prized odor properties, amongst the ensemble of possible stereoisomers.

THE INVENTION

The present invention thus brings an original solution to the problem of obtaining this fragrance speciality. The particular object of the invention is a process, the key step of which consists in the preparation of acetylenic compounds of formula

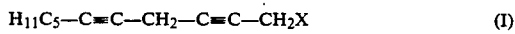

wherein X stands for a bromine or chlorine atom, a hydroxyl group or —NR$_2$, R representing a lower alkyl radical.

Amongst the compounds of formula (I) one can cite the amine compounds (X=—NR$_2$) whose structure is novel and which are also preferred compounds to be used according to an embodiment of the process of the invention.

The process according to the invention rests on a selective synthesis based upon conventional reaction steps, the choice of which, in view of preparing undecatriene, has however never been mentioned, nor even suggested, up until now. Such reactions conform to the high selectivity criteria required for obtaining the preferred isomer in good yield and without having to resort to intricate separation steps.

The process according to the invention comprises the following consecutive steps:
a. conversion of deca-1,4-diyne into a N,N-disubstituted undeca-2,5-diynyl-amine by way of treatment of said deca-1,4-diyne with formaldehyde and a secondary amine under the conditions of a Mannich type reaction; followed by
b. reduction of the thus obtained compound by means of a catalytic hydrogenation to give a N,N-disubstituted undeca-2Z,5Z-dienyl-amine, and
c. an elimination reaction, under the conditions of so-called Hoffmann type reaction, consisting in the quaternarization of the obtained N,N-disubstituted undeca-2Z,5Z-dienyl-amine, conversion into the corresponding ammonium hydroxide and decomposition; or
d. conversion of said N,N-disubstituted undeca-2Z,5Z-dienyl-amine into the corresponding N-oxide; and
e. thermal treatment of the obtained N-oxide to give the desired undeca-1,3E,5Z-triene.

The process defined above can be illustrated by way of the following reaction scheme:

Scheme I

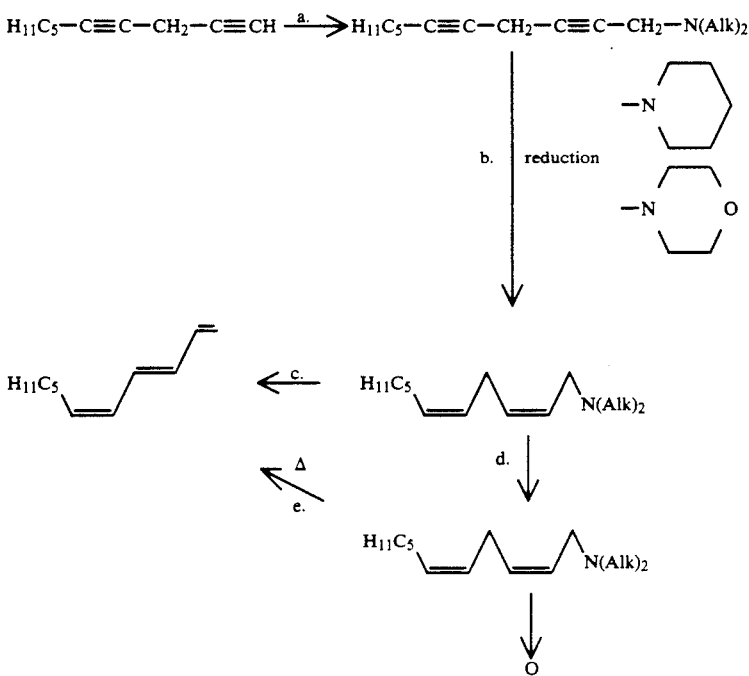

The starting product in the invention process, deca-1,4-diyne, is a compound of known chemical structure, which can be obtained according to a process described in the literature [L. Brandsma, Preparative Acetylenic Chemistry, exp. 34, p. 52, Elsevier (1971)] by way of a Grignard reaction between 1-heptyne and ethylmagnesium bromide, followed by addition of propargyl bromide. On the other hand, the same deca-1,4-diyne can be synthesized according to the method described in Synthesis 1979, 292, starting from propargyl p-toluenesulfonate, which compound is easily obtained from propargyl alcohol [see the method suggested by L. Brandsma, cited ref., exp. 5, p. 159].

The thus obtained deca-1,4-diyne is preferably maintained in solution in an appropriate inert solvent like an ether such as tetrahydrofuran. It was in fact observed that this acetylenic compound is unstable, so that it is therefore advisable to use it according to the invention in a speedy manner.

The first step of the reaction is carried out under the usual conditions applied to a Mannich type reaction [see: Herbert O. House, Modern Synthetic Reactions, 2nd edition, Benjamin Inc. (1972); L. Brandsma, cited ref., exp. 44, p. 59]. As the secondary amine, dialkylamine such as diethylamine can be used. The subsequent hydrogenation step is carried out in a common reactor and in the presence of a current hydrogenation catalyst known for its capability to promote the conversion of the acetylenic bonds into olefins having cis-isomery. A partially poisoned palladium catalyst, so-called of the Lindlar type, is perfectly suitable for this type of reaction [see Fieser and Fieser, Reagents for Organic Synthesis, p. 566 (1967)]. At the time of the hydrogenation, it is necessary to stop the reduction once two hydrogen equivalents have been consumed, so as to prevent the formation of products originating from subsequent hydrogenation of the formed olefin.

The Hoffmann type elimination [see Organic Reactions 1960, 11, 317] which characterizes step c. of the process can be carried out, upon quarternarization of the obtained olefinic amine by means of an alkyl halide, for example methyl iodide, by treating the resulting ammonium salt with potassium tert-butoxide at room temperature. Alternatively, it can be effected by methylation and simultaneous elimination, by way of a treatment with dimethylsulfate in the presence of sodium hydroxide, in refluxing water.

According to a variant of the process of the invention, the N,N-disubstituted undeca-2Z,3Z-dienyl-amine is converted into its corresponding N-oxide derivative and, henceforth, the obtained oxide is subjected to a thermal treatment to give the desired undeca-1,3E,5Z-triene. The formation of said N-oxide can proceed by analogy to the method described by A. C. Cope and E. Ciganek [Organic Synthesis Coll. vol. IV, Rabjohn, p. 612]. The subsequent thermal treatment occurs by pyrolysis at a temperature of about 170°-190° C. This variant just described makes it possible to obtain the desired undecatriene together with equivalent amounts of its undeca-2Z,4Z,6E-triene isomer. These two components can then be separated by any one of the usual techniques.

In addition to the above-described method, the present invention also has as its object the compounds of formula (I) wherein symbol X defines a -NR$_2$ radical, R being a lower alkyl group.

Another object of the invention is a process for obtaining undeca-1,3E,5Z-triene, wherein i. deca-1,4-diyne is reacted with an alkyl magnesium halide and then formaldehyde to give undeca-2,5-diyn-1-ol;

ii. the said diynol is subjected to catalytic hydrogenation to give undeca-2Z,5Z-dienol;

iii. the thus formed dienol is converted into undeca-2Z,5Z-dienyl chloride; and iv. the latter compound is subjected to an elimination reaction by means of a basic agent consisting of an alkali metal alkoxide.

The process described above is illustrated by way of the following reaction scheme:

Scheme II

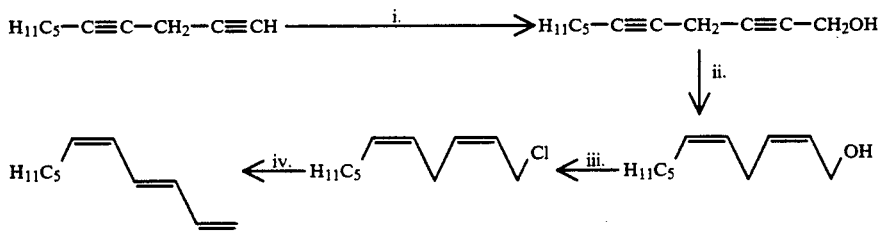

The present invention will now be described in detail by way of the following examples wherein the temperatures are indicated in degrees centigrade and the abbreviations have the usual meaning in the art.

EXAMPLE 1

Deca-1,4-diyne, used as starting product in the process according to the invention, was prepared in the following manner.

Into a 1 l vessel, there were charged 19.2 g of magnesium chips (0.8 mole) into 550 ml of tetrahydrofuran (THF) under nitrogen. To this mixture, there were added dropwise 84 g (0.77 mole) of ethyl bromide so as to maintain the THF in reflux. Once the ethyl magnesium bromide had been formed, 62.4 g (0.65 mole) of 1-heptyne were added dropwise at 10°, over 10 min, and the mixture was heated to 60° for 45 min. After cooling to 10°, 1.93 g (19.5 mmole) of CuCl were added thereto and the mixture was left at rest for 15 min. 138 G (0.65 mole) of propargyl p-toluenesulfonate were then added over 20 min to the reaction mixture maintained at 0°. The latter was left at rest for 30 min while surveying that the temperature did not rise above 5°. It was then heated to 15° to complete the reaction. The reaction mixture was hydrolyzed with 100 ml of water and the aqueous phase was separated and extracted with two fractions of 80 ml THF each. The combined organic extracts were then washed with an aqueous solution saturated with NaCl, two fractions of 50 ml each of a 5% aqueous solution of KCN and was then dried over $Na_2SO_4$. After filtration and evaporation, a concentrated solution of deca-1,4-diyne in THF was obtained, which was used in the following reaction step.

a. 19.5 G (0.65 mole) of paraformaldehyde, 54.8 g (0.75 mole) of diethylamine, 2.6 g of hydrated copper (II) acetate and 65 ml of THF were charged into a 1 l reactor. The mixture was maintained at reflux for 30 min and, still at reflux, the solution of deca-1,4-diyne obtained as described above was added thereto. The reaction mixture was kept at reflux for 1½ h until the deca-1,4-diyne had completely disappeared. The mixture was then extracted at 0° with a 15% solution of HCl (3×70 ml) and the acidic layers were extracted with two fractions of 50 ml each of petroleum ether 80:100°, then 150 ml of a 30% NaOH solution were added thereto at 0°. The basic phase thus obtained was extracted with three fractions of 150 ml each of ethyl acetate and the organic extracts treated with a saturated aqueous solution of NaCl, dried over $Na_2SO_4$, filtered and evaporated to give 105 g of N,N-diethyl-undeca-2,5-diynyl-amine.

IR: 2940, 1460, 1310, 1200, 1090 cm$^{-1}$
$^1$H-NMR: 0.9(3H,t,J=7); 1.07(6H,t,J=7); 1.3-1.55(6H,m); 2.15(2H,m); 2.55(4H,q,J=7); 3.15(2H,m); 3.40(2H,t,J=2.5) δ ppm
MS: M$^+$=219(4); 204(100), 91(30), 58(21)

b. 105 g of the amine prepared as indicated under a. in solution in 500 ml of cyclohexane were placed in a 1.5 l hydrogenation reactor and 2.7 g of Lindlar catalyst and 2 drops of quinoline were added thereto. The hydrogenation was carried out at atmospheric pressure and it was interrupted after absorption of 2 equivalents of hydrogen. Filtration, evaporation and bulb-to-bulb distillation provided 99.8 g of N,N-diethylundeca-2Z,5Z-dienyl-amine.

Yield: 95%; B.p.:60°/2.66 Pa.
IR: 2950, 1650, 1460, 1380, 1200, 1060 cm$^{-1}$
$^1$H-NMR: 0.9(3H,t,J=7); 1.05(6H,t,J=7); 1.3(6H,m); 2.05(2H,q,J=7); 2.53(4H,q,J=7); 2.82(2H,t,J=5); 3.15(2H,d,J=5); 5.37(2H,m); 5.5(2H,t,J=5) δ ppm
MS: M$^+$=223(3); 208(4), 164(5), 150(30), 125(27), 112(100), 110(77), 79(86), 58(75)

c. 4.5 G (20.18 mmole) of the amine obtained under b. in 15 ml of ethyl acetate were placed in a 50 ml flask under nitrogen and 4.26 g (30 mmole) of methyl iodide were added thereto. After having kept the mixture at room temperature for 1 h, the solvent was evaporated under vacuum and 10 ml of tert-butanol were added thereto, followed by, at 5°, 3.36 g (30 mmole) of potassium tert-butylate. The mixture was maintained at room temperature for 20 min, and then 30 ml of water and 30 ml of ethyl acetate were added thereto. After separation, the aqueous phase was retaken with 2 fractions of 10 ml each of ethyl acetate and the organic extracts were washed with an aqueous solution (10 ml) saturated with NaCl, while the pH was adjusted to 5–6 by adding 15 ml of a 10% solution of oxalic acid. After washing again with 10 ml of an aqueous solution saturated with NaCl, 10 ml of a sodium bicarbonate solution and two new fractions of 10 ml each of NaCl, the organic extracts were dried over $Na_2SO_4$, filtered, evaporated and bulb-to-bulb distilled to give 2.34 g (15.13 mmole) of undeca-1,3E,5Z-triene having a purity of about 95%.

Yield: 75%.

Variant

The conversion of N,N-diethyl-undeca-2Z,5Z-diethylamine into undeca-1,3E,5Z-triene can also be carried out in the following manner.

3.9 G (17.5 mmole) of the amine were placed in a 25 ml flask with 2.8 g (70 mmole) of NaOH in solution in 12 ml of water. The mixture obtained was heated to boiling point and then 4.4 g (35 mmole) of dimethylsulfate were added thereto dropwise. After 1 h, a new fraction of 1.4 g of NaOH (35 mmole) and 2.2 g (17.5 mmole) of dimethylsulfate were added. After having been left at reflux for 1 h, the mixture was cooled and extracted with ethyl acetate. Following the extraction method described above under c., 1.8 g (yield: 67%) of the desired undecatriene were obtained, the purity of which was around 95%.

EXAMPLE 2

(see Scheme I, step d.)

d. 4 G (18 mmole) of N,N-diethyl-undeca-2Z,5Z-dienyl-amine in 10 ml of ethanol were placed in a 25 ml flask under nitrogen and 4 ml of 70% oxygenated water were added thereto. The reaction mixture was maintained under stirring for 1 h and then left to rest at room temperature for 18 h. After evaporation, it was retaken with ethyl acetate and the organic phase, once separated, was washed with a saturated solution of NaCl, dried over $Na_2SO_4$ and evaporated to provide 4.09 g of N,N-diethyl-undeca-2Z,5Z-dienyl-amine N-oxide (yield: 95%).

IR: 2940, 1650, 1460, 1380, 780 cm$^{-1}$ $^1$H-NMR(80 MHz): 0.9(3H,t,J=7); 1.1(6H,t,J=7); 1.3(6H,m); 2.04(2H,m); 2.75(2H,m); 3.33(4H,q,J=7); 3.95(2H,d,J=5); 5.3(2H,m); 5.65(2H,m) δ ppm MS: M$^+$=239(1); 151(8), 109(18), 95(39), 89(92), 81(50), 74(100), 67(67), 55(49), 41(36)

(see Scheme I, step e.)

e. the N-oxide obtained under d. above was distilled in a bulb-to-bulb apparatus at 180° and atmospheric pressure to give 2.48 g (16.5 mmole) of at 1:1 mixture of undeca-1,3E,5Z-triene and undeca-2Z,4Z,6E-triene.

EXAMPLE 3

(see Scheme II, step i.)

i. A solution of deca-1,4-diyne in THF was prepared following the method indicated in Example 1 and then an equivalent of ethylmagnesium bromide was added thereto at 0°. The mixture was kept at 60° for 45 min. After having added 1,2 equivalent of paraformaldehyde, the mixture was brought to reflux for 3 h. Once cooled, it was extracted with petroleum ether 80:100° and the organic phases were washed with water, then with an aqueous solution saturated with NaCl, dried and evaporated. The obtained residue was chromatographed on a column filled with silica, using as eluting agent a mixture of 1 to 10% of ethyl acetate in cyclohexane. Undeca-2,5-diyn-1-ol was thus obtained in 40% yield.

IR: 3350, 2940, 2200, 1460, 1320, 1010 cm$^{-1}$ $^1$H-NMR: 0.9(3H,t,J=7); 1.25–1.55(6H,m); 2.15(2H,m); 3.20(2H,t,J=2.5); 4.26(2H,t,J=2.5) δ ppm MS: M$^+$=164(1); 131(17), 115(23), 105(29), 95(86), 91(97), 79(100), 77(89), 67(52), 55(42), 41(61)

(see Scheme II, step ii.)

ii. 6.2 G (37.8 mmole) of the carbinol obtained as indicated under letter i. above, dissolved in 50 ml of cyclohexane, were hydrogenated at atmospheric pressure in the presence of 120 mg of Lindlar type palladium catalyst. After filtration and evaporation, the obtained residue was chromatographed on a silica column, using as eluting agent a mixture of 1 to 10% ethyl acetate in cyclohexane, to give 5.9 g (yield: 95%) of undeca-2Z,5Z-dienol.

IR: 3350, 2930, 1460, 1040 cm$^{-1}$ $^1$H-NMR: 0.9(3H,t,J=7); 1.3(6H,m); 2.05(2H,q,J=7); 2.83(2H,t,J=7); 4.22(2H,d,J=7); 5.3–5.45(2H,m); 5.5–5.65(2H,m) δ ppm

MS: M$^+$=168(1); 150(10), 91(30), 79(100), 67(57), 55(50), 41(63)

(see Scheme II, step iii.)

iii. 4.8 g (28.6 mmole) of the olefinic alcohol obtained under letter ii. above were kept at reflux for 1 h in 80 ml of $CCl_4$ in the presence of 11.3 g (43 mmole) of triphenylphosphine. After evaporating the solvent, the residue was filtered on a column filled with silica, using as eluting agent a mixture of 1 to 5% of ethyl acetate in cyclohexane, to give 4.16 g of undeca-2Z,5Z-dienyl chloride (yield: 78%).

IR: 2940, 1460 cm$^{-1}$ $^1$H-NMR(80 MHz): 0.9(3H,t,J=7); 1.3(6H,m); 2.05(2H,q,J=7); 2.88(2H,t,J=7); 4.13(2H,d,J=7); 5.33(1H,m); 5.44(1H,m); 5.63(2H,m) δ ppm $^{13}$C-NMR: 15.37(q); 23.9(t); 26.9(t); 28.6(t); 30.6(t); 32.9(t); 40.65(t); 126.7(d); 127.6(d); 132.9(d); 135.0(d) δ ppm MS: M$^+$=186(1); 150(8), 116(10), 102(32), 91(30), 79(68), 67(100), 55(47), 41(28)

(see Scheme II, step iv.)

iv. The raw undeca-2Z,5Z-dienyl chloride, such as obtained as indicated above, was diluted in 15 ml of tert-butanol and 3.36 g (30 mmole) of potassium tert-butylate were added thereto at 0°. After stirring the mixture for 1 h, it was extracted and treated as described in Example 1, letter c., to give, in 72% yield, a mixture containing 95% of undeca-1,3E,5Z-triene together with 4% of undeca-1,3Z,5E-triene.

What I claim is:

1. Process for the preparation of undeca-1,3E,5Z-triene, comprising the following consecutive steps:
   a. converting deca-1,4-diyne into a N,N-disubstituted undeca-2,5-diynyl-amine by treating said deca-1,4-diyne with formaldehyde and a secondary amine; followed by
   b. reducing the thus obtained compound by catalytic hydrogenation to give a N,N-disubstituted undeca-2Z,5Z-dienyl-amine; and
   c. quaternarizing the N,N-disubstituted undeca-2Z,5Z-dienyl-amine by an alkyl halide or an alkyl sulfate to form an ammonium salt, followed by treating the ammonium salt with a base to obtain the desired undeca-1,3E,5Z-triene.

2. Process according to claim 1, wherein diethylamine is used as the secondary amine in reaction step a.

3. Process according to claim 1, wherein the catalytic hydrogenation according to step b. is carried out in the presence of a partially poisoned palladium catalyst.

4. Process according to claim 1, wherein quaternarizing of N,N-disubstituted undeca-2Z,5Z-dienyl-amine by an alkyl halide, followed by treating with potassium tert-butylate, or by methylating and simultaneously eliminating with dimethyl sulfate in the presence of sodium hydroxide at reflux.

5. Process for the preparation of undeca-1,3E,5Z-triene, by:
   i. reacting deca-1,4-diyne with an alkyl magnesium halide and then formaldehyde to give undeca-2,5-diyn-1-ol;
   ii. subjecting the diynol to catalytic hydrogenation to give undeca-2Z,5Z-dienol;
   iii. converting the dienol into undeca-2Z,5Z-dienyl chloride; and
   iv. subjecting the dienyl chloride to an elimination reaction by a alkali metal alkoxide basic agent.

6. Process according to claim 5, wherein potassium tert-butoxide is used as the alkali metal alkoxide.

7. Process for the preparation of undeca-1,3E,5Z-triene, comprising the following consecutive steps:

a. converting deca-1,4-diyne to a N,N-disubstituted undeca-2,5-diynyl-amine by treating said deca-1,4-diyne with formaldehyde and a secondary amine; followed by
b. reducing the thus obtained compound by catalytic hydrogenation to give a N,N-disubstituted undeca-2Z,5Z-dienyl-amine;
c. converting the N,N-disubstituted undeca-2Z,5Z-dienyl-amine into the corresponding N-oxide; and
d. thermally treating the N-oxide to give the desired undeca-1,3E,5Z-triene.

8. Process according to claim 7, wherein diethylamine is used as the secondary amine and N,N-diethyl-undeca-2,5-dienyl-amine is obtained according to reaction step a.

9. Process according to claim 7, wherein the catalytic hydrogenation according to step b. is carried out in the presence of a partially poisoned palladium catalyst.

* * * * *